(12) United States Patent
Dorssers et al.

(10) Patent No.: US 6,500,417 B1
(45) Date of Patent: *Dec. 31, 2002

(54) MUTANTS OF HUMAN INTERLEUKIN-3

(75) Inventors: Lambertus Christiaan Johannes Dorssers, An Randwijk (NL); Robert Willem van Leen, A/D Ijssel (NL)

(73) Assignee: DSM N.V., Delft (NL)

( * ) Notice: Subject to any disclaimer, the term of this patent is extended or adjusted under 35 U.S.C. 154(b) by 0 days.

This patent is subject to a terminal disclaimer.

(21) Appl. No.: 08/569,284

(22) Filed: Dec. 8, 1995

Related U.S. Application Data

(63) Continuation of application No. 08/150,331, filed on Nov. 8, 1993, now Pat. No. 5,516,512, which is a continuation of application No. 07/651,437, filed on Feb. 5, 1991, now abandoned, which is a continuation-in-part of application No. 07/517,653, filed on May 3, 1990, now abandoned.

(30) Foreign Application Priority Data

| Aug. 14, 1989 | (EP) | ............................................. | 89202082 |
| Sep. 14, 1989 | (EP) | ............................................. | 89202331 |
| Aug. 2, 1990 | (EP) | ............................................. | 90202117 |

(51) Int. Cl.$^7$ .......................... A61K 45/00; C12P 21/04; C12N 1/20; C12N 15/74
(52) U.S. Cl. ...................... 424/85.2; 530/351; 536/23.5; 435/320.1; 435/325; 435/252.3; 435/254.11; 435/69.52
(58) Field of Search ........................ 530/351; 424/85.2; 536/23.5; 435/320.1, 325, 252.3, 254.11, 69.52, 471

(56) References Cited

U.S. PATENT DOCUMENTS

| 4,959,455 A | 9/1990 | Clark et al. .................. 530/351 |
| 5,516,512 A * | 5/1996 | Dorssers et al. ............ 424/85.2 |

FOREIGN PATENT DOCUMENTS

| EP | 0282185 | 9/1988 |
| WO | 8800598 | 1/1988 |
| WO | 8804691 | 6/1988 |
| WO | 8805469 | 7/1988 |

OTHER PUBLICATIONS

Cunningham BC and Wells JA. High–resolution epitope mapping of hGH–receptor interactions by alanine–scanning mutagenesis. Science. Vo. 244, pp. 1081–1085, 1989.*
Yang et al., *Cell* (1986) 47:3–10.
Dorssers et al., *Gene* (1987) 55:115–124.
Moonen et al., *Proc. Natl. Acad. Sci.* (1987) 84:4428–4431.
Kaushansky et al., *Proc. Natl. Acad. Sci.* (1989) 86:1213–1217.
Gough et al., *Eur. J. Biochem.* (1987) 169:353–358.
Kuga et al., *Biochem. Biophys. Res. Commun.* (1989) 159:103–111.
Makino et al., *Proc. Natl. Acad. Sci.* (1987) 84:7841–7845.
Wang et al., *Science* (1984) 224:1431–1433.
Cohen et al., *Science* (1986)234:349–352.
Zurawski et al., *EMBO J.* (1988) 7:1061–1069.
Robb et al., *Proc. Natl. Acad. Sci.* (1988) 85:5654–5658.
Collins et al., *Prac. Natl. Acad. Sci.* (1988) 85:7709–7713.
Clark–Lewis et al., *Proc. Natl. Acad. Sci.* (1988) 85:7897–7901.
Clark–Lewis et al., *Science* (1986) 231:134–139.
Mosely et al., *Proc. Natl. Acad. Sci.* (1984) 84:4572–4576.
Kaushansky et al., *J. Clin. Invest.* (1992) 90:1879–1888.
Dunbar et al, *Science* (1989) 245:1493–1496.

* cited by examiner

*Primary Examiner*—Gary L. Kunz
*Assistant Examiner*—Robert S. Landsman
(74) *Attorney, Agent, or Firm*—Morrison & Foerster LLP

(57) ABSTRACT

Biologically active deletion and substitution mutants of hIL-3 are provided. Preferred mutants are those having one or more deletions at the N-terminus (amino acids 1–14) and/or the C-terminus (amino acids 116–133, 120–130 and/or 130–133). Preferred substitution mutants include $Cys^{16} \rightarrow Ala^{16}$ and/or $Cys^{84} \rightarrow Ala^{84}$, $Glu^{50} \rightarrow Lys^{50}$ and $Lys^{79} \rightarrow Glu^{79}$. These mutants can be used to formulate pharmaceutical compositions. Also disclosed are antibodies directed against specific epitopes localized between amino acids 29 and 54.

18 Claims, 5 Drawing Sheets

```
 -12  met thr met ile thr asn ser arg gly ser val asp Ala Pro Met Thr    4
   1  ATG ACC ATG ATT ACG AAT TCC CGG GGA TCC GTC GAC GCT CCC ATG ACC   48

5  Gln Thr Thr Pro Leu Lys Thr Ser Trp Val Asn Cys Ser Asn Met Ile   20
  49  CAG ACA ACG CCC TTG AAG ACA AGC TGG GTT AAC TGC TCT AAC ATG ATC   96

21  Asp Glu Ile Ile Thr His Leu Lys Gln Pro Pro Leu Pro Leu Leu Asp   36
  97  GAT GAA ATT ATA ACA CAC TTA AAG CAG CCA CCT TTG CCT TTG CTG GAC  144

37  Phe Asn Asn Leu Asn Gly Glu Asp Gln Asp Ile Leu Met Glu Asn Asn   52
 145  TTC AAC AAC CTC AAT GGG GAA GAC CAA GAC ATT CTG ATG GAA AAT AAC  192

53  Leu Arg Arg Pro Asn Leu Glu Ala Phe Asn Arg Ala Val Lys Ser Leu   68
 193  CTT CGA AGG CCA AAC CTG GAG GCA TTC AAC AGG GCT GTC AAG AGT TTA  240

69  Gln Asn Ala Ser Ala Ile Glu Ser Ile Leu Lys Asn Leu Leu Pro Cys   84
 241  CAG AAC GCA TCA GCA ATT GAG AGC ATT CTT AAA AAT CTC CTG CCA TGT  288

85  Leu Pro Leu Ala Thr Ala Ala Pro Thr Arg His Pro Ile His Ile Lys  100
 289  CTG CCC CTG GCC ACG GCC GCA CCC ACG CGA CAT CCA ATC CAT ATC AAG  336

101  Asp Gly Asp Trp Asn Glu Phe Arg Arg Lys Leu Thr Phe Tyr Leu Lys  116
 337  GAC GGT GAC TGG AAT GAA TTC CGG AGG AAA CTG ACG TTC TAT CTG AAA  384

117  Thr Leu Glu Asn Ala Gln Ala Gln Gln Thr Thr Leu Ser Leu Ala Ile  132
 385  ACC CTT GAG AAT GCG CAG GCT CAA CAG ACG ACT TTG AGC CTC GCG ATC  432

133  Phe ***
 433  TTT TGA GTC CAA CGT CCA GCT CGT TCT CTG GGC CTT CTC ACC ACA GAG  480

481  CCT CGG TCG AGT TTT AAA CTG GTT CCT AGG GAT GTG TGA GAA TAA ACT  528

529  AGA CTC TGA ACA AAA AAA AAA AAA AAA AAA AAA AAA AAA AAA AAC CGA  576

577  ATT CCC GGG GAT CTA AAC TT
```

FIG. 1

```
          5'
 -15  met thr met ile thr asn ser arg gly ser ser ala ala ala ala Ala    1
   1  ATG ACC ATG ATT ACG AAT TCC CGG GGA TCC TCT GCA GCA GCG GCG GCT   48

...  ................................................................. ..

3'
 130  Leu Ala Ile Phe ***
 433  CTC GCG ATC TTT TGA CTC GAG TAG AAG AGA AGA GAA TC
```

MUTANTS OF HUMAN INTERLEUKIN-3

CROSS-REFERENCE TO RELATED APPLICATION

This application is a continuation of U.S. Ser. No. 08/150,331 filed Nov. 8, 1993 now U.S. Pat. No. 5,516,512, which is a continuation of U.S. Ser. No. 07/651,437 filed Feb. 5, 1991, now abandoned, which is a continuation-in-part of U.S. Ser. No. 07/517,653 filed May 3, 1990, and now abandoned. The contents of these applications are incorporated herein by reference.

TECHNICAL FIELD

The present invention relates to mutants of colony stimulating factors, obtained by recombinant DNA techniques. More specifically, the invention relates to mutants of interleukin-3, containing one or more deletions and/or one or more substitutions, with interesting pharmacological properties.

BACKGROUND OF THE INVENTION

Historically, factors affecting hematopoietic cells have been detected in an assay measuring the proliferation and/or differentiation of bone marrow cells in soft agar cultures. The factors showing this activity have been collectively called colony-stimulating factors (CSFs). More recently, it has been found that a variety of CSFs exist which, in part, can be classified by the hematopoietic lineages that are stimulated.

In human and murine systems, these proteins include G-CSF and M-CSF. These proteins stimulate the in vitro formation of predominantly neutrophilic granulocyte and macrophage colonies, respectively. Interleukin-2 ("IL-2") stimulates the proliferation of both activated T-cells and activated B-cells, but is not considered a colony stimulating factor.

GM-CSF and interleukin-3 ("IL-3", also known as "Multi-CSF") stimulate the formation of macrophage and both neutrophilic and eosinophilic granulocyte colonies. In addition, IL-3 stimulates the formation of mast, megakaryocyte and pure and mixed erythroid colonies (D. Metcalf, "The hematopoietic colony-stimulating factors", 1984, Elsevier, Amsterdam, and D. Metcalf, Science 299 (1985) 16–22).

Growth factor-induced cell proliferation is a complicated process. Following highly specific binding of the growth factor to its receptor at the cell surface, the complex is internalized by endocytosis and induces an intracellular response often preceded by phosphorylation of the receptor (Sibley e al., Cell 48 (1987) 913–922). These intracellular signals result in specific gene transcription and finally in DNA synthesis and cell replication.

There is considerable interest in the CSFs, since they may be therapeutically useful for restoring depressed levels of hematopoietic and lymphoid stem cell-derived cells.

Human IL-3 ("hIL-3") is such a CSF. Mature hIL-3 consists of 133 amino acids; the protein contains one disulfide bridge and has two potential glycosylation sites (Yang et al., Cell 47 (1986) 3–10). It has inter alia the following activities:

1) stimulation of colony formation by human hematopoietic progenitor cells wherein the colonies formed include erythroids, granulocytes, megakaryocytes, granulocyte macrophages, and mixtures thereof; and
2) stimulation of DNA synthesis by human acute myelogenous leukemia (AML) blasts.

Useful agonists and antagonists of a protein can be created once the structure-function relationship of the molecule is understood. Generally, this relationship is studied by modifying, replacing or deleting amino acids. In this way, information can be obtained about the importance of each of the amino acids for the activity of the protein. Important domains of proteins may be the active site, metal and cofactor binding sites, receptor binding sites, the amino acids involved in subunit interactions, and the antigenic determinants.

Once the primary sequence of a protein has been determined, various procedures can be employed to study the above-mentioned characteristics. For example, if primary structures of homologous proteins from other species are available, the sequences can be compared. Conserved sequences are often indicative of the importance of certain amino acids.

Secondary structures can be predicted with the use of known algorithms. See, e.g., Hopp and Woods, Proc. Natl. Acad. Sci. USA 78 (1981) 3824–3828, Garnier et al., J. Mol. Biol. 120 (1978) 97–120, Biou et al., Prot. Eng. 2 (1988) 185–191, Carmenes et al., Biochem. Biophys. Res. Commun. 159 (1989) 687–693.

If interspecies homology between homologous proteins is high and the 3-D structure of one of them is known, important amino acids can also be deduced from this structure.

Primary and/or spatial-structure data can be used to make an educated guess for mutagenesis experiments. Expression of mutagenized proteins and the testing of these muteins in biological assays provides information about the relative importance of certain amino acids.

The aim of the present invention is to provide IL-3 mutants with similar or improved pharmaceutical properties with respect to the native IL-3, preferably using the procedures mentioned above.

BACKGROUND LITERATURE

Human Interleukin-3

In 1984, cDNA clones coding for murine IL-3 were isolated (Fung et al., Nature 307 (1984) 233–237 and Yokota et al., Proc. Natl. Acad. Sci. USA 81 (1984) 1070–1074). This cDNA would not hybridize with human DNA or cDNA clones. Thus, it was speculated that a human counterpart for murine IL-3 (mIL-3) did not exist. This belief was reinforced by the wide spectrum of activities of the human GM-CSF. Finally, in 1986, a gibbon cDNA expression library provided the gibbon IL-3 sequence. This sequence was subsequently used as a probe against a human genomic library. This provided evidence for the presence of IL-3 in human beings (Yang et al., Cell 47 (1986) 3–10).

Meanwhile, Dorssers et al., Gene 55 (1987) 115–124, found a clone from a human cDNA library that surprisingly hybridized with mIL-3. This hybridization was the result of the high degree of homology between the 3' noncoding regions of mIL-3 and hIL-3.

Modified CSFs (other than IL-3)

Moonen e al., Proc. Natl. Acad. Sci. USA 84 (1987) 4428–4431 describe the production of human GM-CSF by several recombinant sources including *E. coli*, yeast and animal cells. Partially purified expression products from yeast and animal cells were assayed for the effect of deglycosylation. The immunoreactivity was increased 4- to 8-fold upon removal of the N-linked oligosaccharides. The specific biological activity was increased by a factor of 20, both in the chronic myelogenous leukemia (CML) and in the human bone marrow assay.

Kaushansky e a., Proc. Natl. Acad. Sci. USA 86 (1989) 1213–1217, tried to define the region(s) of the GM-CSF polypeptide required for biological activity. Since human and murine GM-CSF do not cross-react in their respective colony-forming assays, the approach was based on the use of hybrid DNA molecules containing various lengths of the coding regions for h- and mGM-CSF. After expression in COS cells, the hybrid proteins were tested in both human and murine colony-forming assays. Two regions of GM-CSF were found to be critical for hematopoietic function. These regions are structurally characterized by an amphiphilic helix and by a disulfide-bonded loop.

Gough et al., Eur. J. Biochem. 169 (1987) 353–358, describe internal deletion mutants of murine GM-CSF. None of the mutants is reported to show biological activity.

Kuga et al., Biochem. Biophys. Res. Com. 159 (1989) 103–111, describe mutagenesis of human G-CSF. The results indicate that most of the expression products with mutations localized in the internal or C-terminal regions abolish hG-CSF activity. On the other hand, N-terminal deletion mutants missing 4, 5, 7 or 11 amino acids, out of a total of 174 amino acids, retained activity. Some of the N-terminal amino acid mutants showed increased activity.

Deletion mutants of human interleukin-1 (IL-1) have been created using available endonuclease restriction sites and expression in eukaryotic cells. The carboxyl terminal third (63 amino acids) of the polypeptide contains the active site (Makino et al., Proc. Natl. Acad. Sci. USA 84 (1987) 7841–7845). A recent study on IL-1alpha and IL-1beta shows that 140 and 147 amino acids, respectively (out of a total of 153 amino acids), are required for full biological activity (Mosley et al., Proc. Natl. Acad. Sci. USA 84 (1987) 4572–4576). Single amino acid changes at both termini result in significant decrease of biological activity. However, no detailed information with respect to the receptor-binding domain of IL-1 has been obtained from these studies.

Activity of human interleukin-2 was shown to be severely inhibited by removal of both $Cys^{58}$ and $Cys^{105}$ whereas deletion of the third Cys residue (125) had no effect (Wang et al., Science 224 (1984) 1431–1433; Cohen et al., Science 234 (1986) 349–352). All substitutions resulting in a disturbance of helical folding of this protein were found to give significant reductions of biological activity. The potential receptor binding site of IL-2 has been mapped on an eleven amino acid long peptide. Individual amino acid substitutions in this region had dramatic effects (Cohen et Al., (supra); Zurawski and Zurawski, EMBO J. 7 (1988) 1061–1069). Mutational analysis further revealed that different domains of IL-2 are involved in high and low affinity binding of the IL-2 receptor complex (Robb et al., Proc. Natl. Acad. Sci. USA 85 (1988) 5654–5658; Collins et al., Proc. Natl. Acad. Sci. USA 85 (1988) 7709–7713).

Modified IL-3

Clark-Lewis et Al., Science et al., (1986) 134–139, performed a functional analysis of synthetic murine IL-3 analogs. They concluded that the stable tertiary structure of the complete molecule was required for full activity. A study on the role of the disulfide bridges showed that replacement of two of the four Cys residues by Ala ($Cys^{79}$, $Cys^{140} \rightarrow Ala^{79}$, $Ala^{140}$) resulted in increased activity (Clark-Lewis et al., Proc. Natl. Acad. Sci. USA 85 (1988) 7897–7901).

Literature on proposed and actually performed modifications of hIL-3 is scarce. International Patent Application (PCT) WO 88/00598 discloses a $Ser^{27} \rightarrow Pro^{27}$ replacement. (It should be noted that the numbering of amino acids in WO 88/00598 includes the signal peptide of 19 amino acids.) Furthermore, suggestions are made to replace Cys with Ser, breaking the disulfide bridge, and to replace one or more amino acids at the glycosylation sites ($Asn^{34}cys^{35}Ser^{36}$ and $Asn^{89}Ala^{90}Ser^{91}$).

EP-A-0275598 (WO 88/04691) illustrates that $Ala^1$ can be deleted while retaining biological activity. Some mutant hIL-3 sequences are provided, viz. two double mutants, $Ala^1 \rightarrow Asp^1$, $Trp^{13} \rightarrow Arg^{13}$ (pGB/IL-302) and $Ala^1 \rightarrow Asp^1$, $Met^3 \rightarrow Thr^3$ ((pGB/IL-304) and one triple mutant $Ala^1 \rightarrow Asp^1$, $Leu^9 \rightarrow Pro^9$, $Trp^{13} \rightarrow Arg^{13}$ (pGB/IL-303).

WO88/05469 describes deglycosylation mutants and mutants of $Arg^{54}Arg^{55}$ and $Arg^{108}Arg^{109}Lys^{110}$ (converted to the same numbering as in EP-A-0275598). The latter are suggested in order to avoid proteolysis upon expression in *Saccharomyces cerevisiae* by KEX2 protease. No mutated proteins are disclosed. Glycosylation and the KEX2 protease activity are only important, in this context, upon expression in yeast.

Finally, EP-A-0282185 describes various mutants that may be conformationally and antigenically neutral. To achieve this, a series of synonymous amino acid substitutions are suggested. The proposed changes are aimed at keeping the structure and charge distribution of the IL-3 molecule unaltered. However, the only actually performed mutations are $Met^2 \rightarrow Ile^2$ and $Ile^{131} \rightarrow Leu^{131}$. It is not disclosed whether the contemplated neutralities are obtained.

No known extensive mutagenesis experiments on hIL-3 have been disclosed to date.

The present invention provides new classes of pharmacologically interesting compounds, viz. deletion and substitution mutants of hIL-3, showing biological activities similar and in some cases possibly antagonistic to those of hIL-3.

SUMMARY OF THE INVENTION

In one aspect of the invention, biologically active polypeptide analogs of human interleukin-3 (also referred to hereinafter as "hIL-3 mutants" or "muteins") are provided having a deletion of at least two amino acids.

Preferred mutants are those having one or more deletions at the N-terminus (amino acids 1–14) and/or the C-terminus (amino acids 120–130 and/or 130–133).

In another aspect of this invention, substitution mutants of hIL-3 are disclosed having at least one of the following substitutions:

$Asp^{21}Glu^{22} \rightarrow Lys^{21}Arg^{22}$
$Asp^{36} \rightarrow Arg^{36}$
$Glu^{43}Asp^{44} \rightarrow Lys^{43}Arg^{44}$
$Arg^{54}Arg^{55} \rightarrow Glu^{54}Asp^{55}$
$Asp^{46} \rightarrow Lys^{46}$ or $Arg^{46}$
$Glu^{50} \rightarrow Lys^{50}$ or $Arg^{50}$,
$Glu^{59} \rightarrow Lys^{59}$ or $Arg^{59}$
$Glu^{59} \rightarrow Gly^{59}$ or $Pro^{59}$,
$Arg^{63}Ala^{64} \rightarrow Pro^{63}Gly^{64}$
$Glu^{75} \rightarrow Arg^{75}$ or $Gly^{75}$
$Lys^{79} \rightarrow Glu^{79}$
$Arg^{94} \rightarrow Pro^{94}$
$His^{98}Lys^{100}Asp^{101} \rightarrow Glu^{98}Asp^{100}Gln^{101}$
$Glu^{106} \rightarrow Lys^{106}$
$Arg^{108}Arg^{109}Lys^{110} \rightarrow Glu^{108}Asp^{109}Glu^{110}$,
$Phe^{113}Tyr^{114} \rightarrow Ala^{113}Thr^{114}$ Cys$^{16}$→Ala$^{16}$
Cys$^{84}$→Ala$^{84}$
Cys$^{16}$ Cys$^{84}$→Ala$^{16}$ Ala$^{84}$ In yet another aspect of this invention, antagonists of hIL-3 are disclosed. These antagonists are substitution mutants of hIL-3 that are more potent in receptor binding than in stimulation of DNA synthesis. More specifically, the antagonists are single or double Cys mutants. Preferably Cys is replaced by Ala (Cys$^{16}$→Ala$^{16}$, Cys$^{16}$Cys$^{84}$→Ala$^{16}$Ala$^{84}$). Other mutants having an antagonistic effect are Glu$^{50}$→Lys$^{50}$ and Lys$^{79}$→Glu$^{79}$.

The polypeptides are obtained through expression of suitably modified DNA sequences. Thus, the present invention also provides suitable expression vectors and host cells compatible therewith.

In yet other aspects, the invention comprises pharmaceutical compositions that include biologically active peptide analogs of hIL-3 as described above, in combination with a pharmaceutically acceptable carrier.

Finally, the present invention discloses monoclonal antibodies aimed at an epitope localized between amino acids 29 and 54.

Other embodiments of the subject invention are readily determined by one skilled in the art.

BRIEF DESCRIPTION OF THE DRAWINGS

FIG. 1 SEQ ID NO:45 and SEQ ID NO:46 shows the nucleotide and translated amino acid sequence of the fusion protein insert of pGB/IL-336. Amino acids indicated with lower case letters are non-hIL-3 amino acids. The IL-3 protein sequence begins at Ala1.

FIG. 2 SEQ ID No:47 and SEQ ID NO:48 shows the 5' and 3' sequence changes introduced to obtain pGB/IL-339. Lower case letters indicate non-hIL-3 amino acids. The mature IL-3 sequence begins at Ala1.

DETAILED DESCRIPTION OF THE INVENTION

Figure 3:
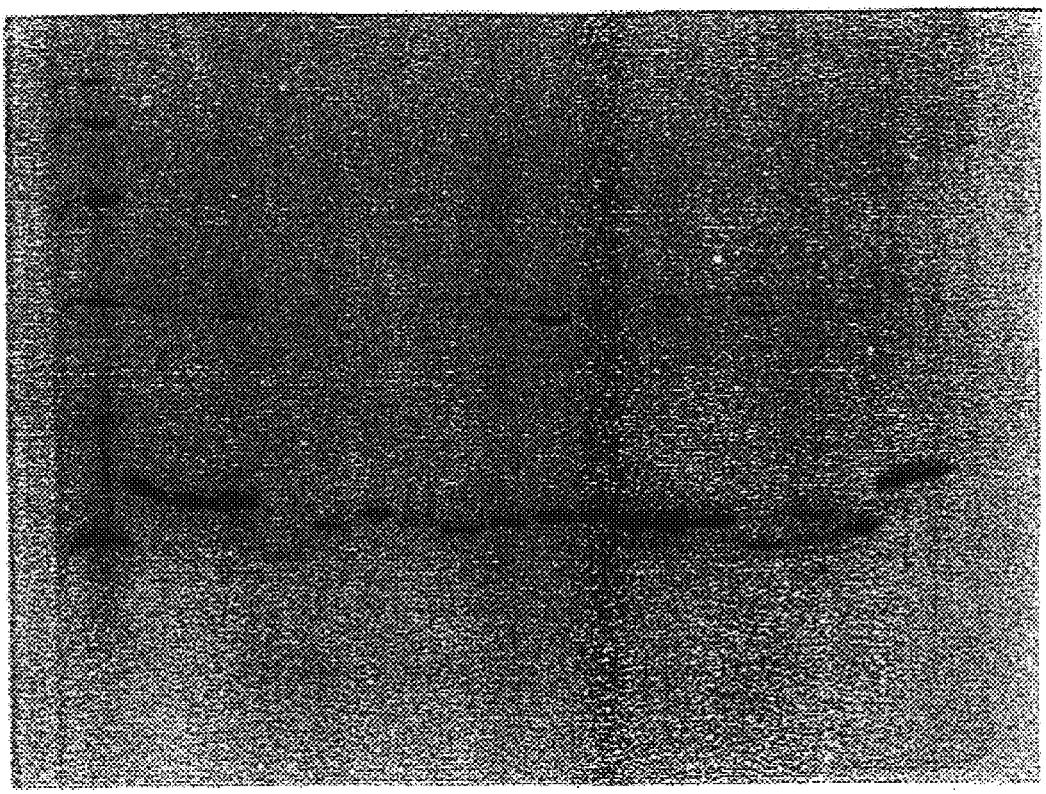
FIG. 3 is a photograph of the polyacrylamide gel of the following 19 IL-3 mutants (lanes 1 to 19 respectively): pGB/IL-336, pGB/IL-339, 932, 810, 934, 812, 935, 813, 936, 820, 937, 821, 938, 822, 939, 9329, 904, 905, 9045; and the Pharmacia LMW marker (lane 20). Mutations corresponding with these numbers are given in Table 4.

As used herein, "human IL-3" corresponds to the amino acid sequence (1-133) as depicted in FIG. 1. Naturally occurring variants are also included. Furthermore, hIL-3 molecules which are modified post-translationally (e.g., by glycosylation) are also encompassed by the term IL-3. By "derivative" of IL-3 is meant any IL-3 molecule that has been chemically or enzymatically modified, but which retains at least a part of its biological activity.

An "analog" of human IL-3 as used herein refers to a molecule having a sequence which differs from mature IL-3 by one or more deletions or substitutions.

Human IL-3 is further characterized by its biological activity to stimulate colony formation by human hematopoietic progenitor cells. The colonies formed include erythroids, granulocytes, megakaryocytes, granulocyte macrophages and mixtures thereof. The biological activity of hIL-3 can (for the present purpose) be further divided into two parts: signal transduction and receptor binding.

An hIL-3 analog, exhibiting improved properties, is defined herein as an analog having a better signal transduction/receptor binding ratio, where better is dependent on the desired properties—i.e., a higher binding coefficient for an antagonist or an equal or higher biological activity for a deletion mutant. Better can also mean that the polypeptide analog is less susceptible to forming aggregates.

For the present purpose the biological activity of the human IL-3 analogs is determined by DNA synthesis by human acute myelogenous blasts. Furthermore, receptor binding assays are performed with donor leucocytes, patient AML cells or MV4–11 cells.

As explained above, IL-3 is active in both receptor binding and signal transduction. If these activities can be attributed to specific amino acid sequences, which may be either continuous or discontinuous, it may become possible to uncouple the binding and signal transducing activities.

In order to determine the structure-function relationship of hIL-3, the following mutagenesis techniques are inter alia to be considered:

a) replacement of one amino acid by an isosteric residue of different function—e.g., Asp by Asn. This maintains the hydrogen bonding characteristics, while removing the charge;

b) replacement of one amino acid by another of identical function but different structure—e.g., Glu by Asp, where a carboxyl group would be moved by about 1 Angstrom;

c) replacement of one amino acid by another of different function;

d) introduction or removal of disulfide bridges;

e) construction of deletion mutants;

f) introduction of helix breakers (e.g. Pro);

g) construction of insertion mutants;

h) generation of glycosylation mutants.

One aspect of the present invention is the development of a specific antagonist which blocks the receptor by binding specifically to it, preferably with a high binding coefficient, thereby hindering the signal transduction.

An antagonist can be any chemical molecule that binds to the receptor and thereby avoids binding of the agonist. The present invention specifically aims at proteins having such a blocking effect. In one of its aspects, the present invention provides an hIL-3 mutein which may have at least a partial antagonist effect. More specifically, these are single or double Cys mutants. Preferably, cys is replaced by Ala (Cys$^{16}$→Ala$^{16}$, Cys$^{16}$ Cys$^{84}$→Ala$^{16}$Ala$^{84}$). Other mutants having an antagonistic effect are Glu$^{50}$→Lys$^{50}$ and Lys$^{79}$→Glu$^{79}$. It may be envisaged that administration of significant doses of the described mutants will prevent the physiological availability of IL-3.

In another aspect of the present invention, there are provided proteins having hIL-3 or hIL-3-like activity, which are smaller, preferably from about 3 to about 25%, than the native hIL-3 molecule. As is further illustrated by the Examples, it can be determined by introducing specific deletions which part of the molecule is indispensable for receptor binding and signal transduction.

The properties of the naturally occurring or naturally mutated IL-3 may be altered by introducing a variety of mutations in the protein. Such alterations are suitably introduced using the mutagenesis techniques described herein and the mutated molecules (hIL-3 muteins) are suitably synthesized using the expression vectors described below.

Two kinds of mutants have specifically been made; a) deletion mutants and b) substitution mutants. It is to be understood that combinations of these mutants can easily be obtained by the described methods.

Deletion mutants have been made, together covering virtually the complete coding region. Deletions, as used herein, can be any amino acid deletion of minimally two consecutive (or separated) amino acids. Preferably, four or more amino acids can be deleted. The deletions can start with any amino acid in the molecule (except near the C-terminus). It is also possible to have two separated deletions in the molecule (e.g., two times one amino acid deletion, two times two, etc.). In a preferred embodiment, 32 amino acids are deleted, 14 at the N-terminus and 18 at the C-terminus of the protein. Surprisingly, all of the expressed deletion mutant proteins showed biological activity.

Four such mutants include an N-terminal deletion mutant missing amino acids 1 to 14, a C-terminal deletion mutant missing amino acids 120 to 130, a double mutant missing amino acids 1 to 14 and 120 to 130 and a C-terminal mutant missing amino acids 130 to 133. These mutants retained 100 percent of both the biological and the binding activity. It is surprising that hIL-3, missing 25 amino acids (20% of the full length hIL-3), still retains 100% of its activity. In view of $cys^{16}$, which is involved in the formation of a disulfide bridge, it is expected that a −15 N-terminal deletion mutant also retains its activity.

The double deletion mutant lacking the 14 amino terminal and up to 18 C-terminal amino acids (Table 4, X and Z), still retains full activity. Such mutants, lacking 32 amino acids, miss at most about 25% of the native molecule. Since this double mutant is fully active, it is expected that the −18 C-terminal mutant will also be fully active.

Internal deletion mutants have also been made. One such mutant which retains complete activity lacks amino acids 120 to 130 (Table 4, 939). It is likely that more such mutants can be made. For processing reasons it may be advantageous to retain the first few amino acids of the mature IL-3 protein. Since the −14 N-terminal deletion mutant retains full activity, it is expected that an internal deletion mutant in the N-terminal region will also retain its activity. Another successful internal deletion might be introduced in the $Gln^{29}$-$Leu^{35}$ region. Additionally, deletion of 1 to 7 amino acids, possibly in combination with a $Lys^{28} \rightarrow Pro^{28}$ substitution, may provide other biologically active mutants.

The discovery that the activity of hIL-3 is retained in the disclosed double mutants or for any other mutant lacking a large part of the protein (e.g., approximately 25 percent) has another potential advantage. A pharmaceutical composition containing hIL-3 can be administered parenterally, intravenously or subcutaneously. The use of a hydrogel composed of biodegradable polymer enclosing the polypeptide and continuously releasing said polypeptide is limited by the amount of peptide that can be enclosed. Using a deletion mutant of the polypeptide with higher specific activity implies that, on a molar basis, more of the active substance can be enclosed in the same volume, thereby increasing the time between successive administrations or possibly avoiding repeated administrations.

It is also possible to introduce specific mutations at the DNA level thereby introducing amino acid substitutions into the encoded protein. These substitutions may be introduced in important conformational or activity regions. An example of such a mutation is a mutation disturbing the disulfide bridge present between $Cys^{16}$ and $Cys^{84}$. By replacing either (or both) of the cysteine residues by an alanine, the bridge cannot be formed, resulting in heavily decreased activity. All three of these mutants have been made and show a relatively high binding activity (with respect to biological activity) in a receptor binding assay.

Since different ratios of relative binding activity to relative biological activity (Table 4) are found, it may be advantageous to use combinations of the disclosed IL-3 analogs. Furthermore, it may be advantageous to use polypeptide analogs having both one or more deletions and one or more substitutions.

Breaking of the disulfide bridge results in a substantial change in the 3D structure of the subject protein; other amino acid substitutions will also influence this structure and hence the activity.

Secondary structure measurements (circular dichroism) show that the hIL-3 molecule has a high percentage (70% at 20° C.) of alpha-helices. Secondary structure prediction programs (i.e., Hopp and Woods, Proc. Natl. Acad. Sci. USA 78 (1981) 3824–3828; Garnier et al., J. Mol. Biol. 120 (1978) 97–120; Biou et al., Prot. Eng. 2 (1988) 185–191; Carmenes et al., Biochem. Biophys. Res. Commun. 159 (1989) 687–693) suggest that these alpha-helices are located between the following amino acids: $Met^{19}$-$His^{26}$, $Gly^{42}$-$Arg^{55}$, $Leu^{58}$-$Glu^{69}$, $Ala^{71}$-$Leu^{81}$, $Leu^{87}$-$His^{95}$, $His^{98}$-$Leu^{111}$ and $Leu^{115}$-$Ala^{121}$.

In view of the charge distribution in the alpha-helices and since it is possible that these charges may play an important role in the interaction with the receptor, the following "charge reversal" substitutions are also encompassed by the present invention:

| | | |
|---|---|---|
| $Asp^{21}Glu^{22}$ | → | $Lys^{21}Arg^{22}$ |
| $Asp^{36}$ | → | $Arg^{36}$ |
| $Glu^{43}Asp^{44}$ | → | $Lys^{43}Arg^{44}$ |
| $Arg^{54}Arg^{55}$ | → | $Glu^{54}Asp^{55}$ |
| $Asp^{46}$ | → | $Lys^{46}$ or $Arg^{46}$ |
| $Glu^{50}$ | → | $Lys^{50}$ or $Arg^{50}$ |
| $Glu^{59}$ | → | $Lys^{59}$ or $Arg^{59}$ |
| $Glu^{59}$ | → | $Gly^{59}$ or $Pro^{59}$ (alpha-helix breaker) |
| $Arg^{63}Ala^{64}$ | → | $Pro^{63}Gly^{64}$ |
| $Glu^{75}$ | → | $Arg^{75}$ or $Gly^{75}$ |
| $Lys^{79}$ | → | $Glu^{79}$ |
| $Arg^{94}$ | → | $Pro^{94}$ |
| $His^{98}Lys^{100}Asp^{101}$ | → | $Glu^{98}Asp^{100}Gln^{101}$ |
| $Glu^{106}$ | → | $Lys^{106}$ |
| $Arg^{108}Arg^{109}Lys^{110}$ | → | $Glu^{108}Asp^{109}Glu^{110}$ |
| $Phe^{113}Tyr^{114}$ | → | $Ala^{113}Thr^{114}$. |

Both deletion and substitution mutants can be used to alter the glycosylation sites, thus enabling the production of glycosylated or unglycosylated polypeptides in eukaryotic host cells at will.

The mutants described above have been used in epitope mapping experiments to determine where exposed segments of the molecule, which may be relevant in receptor binding, are located. To achieve this, monoclonal antibodies were prepared against mature hIL-3. These antibodies were used in Western blotting experiments against mutant proteins. At least one antigenic fragment was detected.

The new hIL-3 mutants according to the present invention can be conveniently prepared by site-directed mutagenesis, as well as by a variety of other techniques which are known in the art.

Suitable vectors which are capable of transforming microorganisms, which can express the mutated DNA sequences encoding the desired hIL-3 mutants, include expression vectors comprising the mutated sequences derived from the mature hIL-3 coding sequence, joined to expression regulating regions and terminator regions. These regions are chosen depending on the prokaryotic or eukaryotic host cells used. Preferable hosts include E. coli or Bacillus. However, fungi, yeast cells and tissue culture cells can also be employed (see EP-A-0275598).

Expression vectors for E. coli include pGB/IL-336 and pGB/IL-339, each containing the lacZ promoter. A preferable expression vector for Bacillus is pGB/IL-322, containing the α-amylase promoter and signal peptide, and derivatives thereof. Other suitable vectors for expression in Bacillus are, for example, HpaII promoter containing vectors and derivatives thereof. These and other vectors are described in EPA 0390252, the disclosures of which are incorporated herein by reference in their entirety.

For convenience it may be useful to use expression constructs which are capable of secreting the protein from the host cell. This can be accomplished using Bacillus constructs. Isolation from inclusion bodies, as exemplified here in E. coli, is also possible.

Purification of the polypeptide obtained after expression is dependent on the host cell and the expression construct used. Generally, the purification of hIL-3 muteins can be performed in the same way as the purification of native hIL-3. To obtain highly purified hIL-3 muteins, the following steps can be used; hydrophobic interaction chromatography, followed by anion exchange chromatography and optionally followed by gel filtration. It may also be sufficient to use only one or two of these purification steps. A detailed description of the purification of hIL-3 is disclosed in commonly owned, copending U.S. patent application Ser. No. 494,182, filed Mar. 13, 1990, and EPA 0390252, filed Mar. 15, 1990, the disclosures of which are incorporated herein by reference in their entirety.

Briefly, after expression in E. coli, inclusion bodies containing the protein are isolated. After sonification in 8 M urea, the protein is further purified using anion exchange chromatography. After removal of the urea, filter sterilization yields a protein that can be used for subsequent biological and biochemical characterization. Hydrophobic interaction and anion exchange chromatography, as well as the use of Bacillus as a host strain, in combination with secretion of the polypeptides, yields highly pure proteins. The elution conditions and column materials to be used with a particular mutein can be determined by one skilled in the art.

The subject muteins can be formulated into pharmaceutical compositions by admixture with a pharmaceutically acceptable nontoxic carrier. As explained above, such compositions may be prepared for use for parenteral (subcutaneous, intramuscular or intravenous) administration particularly in the form of liquid solutions or suspensions. The compositions may conveniently be administered in unit dosage form and may be prepared by any of the methods well known in the pharmaceutical art, for example, as described in Remington's Pharmaceutical Sciences, Mack Publishing Company, Easton, Pa. 1970. Formulations for parenteral administration may contain as common excipients sterile water or saline, polyalkylene glycols such as polyethylene glycol, oils of vegetable origin, hydrogenated naphthalenes and the like.

The materials of this invention can be employed as the sole active agent in a pharmaceutical or can be used in combination with other active ingredients. Other active ingredients can be selected, for example, from appropriate hematopoietins, CSFs and interleukins. These include GM-CSF, CSF-1, G-CSF, M-CSF, erythropoietin, IL-1α, IL-1β, IL-2, IL-4-IL-8, and tumor necrosis factor.

A number of tests are available for assaying the biological activity and potency of hIL-3 analogs of the invention. For example, the analog can be tested, using techniques well known in the art, to see if the protein stimulates colony formation by human hematopoietic progenitor cells. The colonies formed include erythroids, granulocytes, granulocyte macrophages, and mixed. Alternatively, the ability of the subject analogs to stimulate DNA synthesis by human acute myelogenous leukemia (AML) blasts, as evidenced, for example, by labeled thymidine uptake, can be used to indicate activity. AML proliferation assays are discussed further below. Finally, biological activity can be determined using an IL-3 receptor assay as described further in the Examples.

The biologically active polypeptide analogs of human IL-3 as provided by the present invention can be used for both therapeutic and diagnostic purposes. Therapeutic uses include the treatment and prevention of malignant and non-malignant disorders. For example, the subject muteins can be used in the treatment of cytopenias and/or immnosuppression due to infections, cytopenias due to chemotherapy and/or irradiation, bone disorders such as bone fractures and osteoporosis, immunodeficiencies due to general anaesthetic procedures, recovery following bone marrow transplantation, adjunct to vaccination and adjunctive therapy of infections.

Below are examples of specific embodiments for carrying out the present invention. The examples are offered for illustrative purposes only, and are not intended to limit the scope of the present invention in any way.

EXPERIMENTAL

Example 1

Construction of Expression Vectors

Construction of gGB/IL-336

In order to produce a polypeptide closely resembling the mature human IL-3, a construct was made lacking the 5' nontranslated and signal peptide encoding sequences. The IL-3 cDNA insert of pLH1 (see EP-A-0275598) was excised with HincII and HindIII, ligated to a synthetic oligonucleotide (SalI-overhang/blunt, 419/420, Table 1) comprising the sequence encoding the N-terminal 14 amino acids of the mature IL-3 and inserted into SalI-HindIII digested pTZ18R (Pharmacia). Following verification of the sequence, the complete insert was transferred to pUC8 for protein production (as described previously in WO 88/04691), resulting in plasmid pGB/IL-335. To allow for direct sequencing and mutagenesis, the PvuI fragment of plasmid pTZ18R carrying the f1-origin of replication was used to replace the corresponding PvuI fragment of pUC8. The resulting bacterial expression plasmid pGB/IL-336 gives rise to a fusion protein of 145 amino acids with a calculated mw of 16,384 dalton (FIG. 1).

Construction of DGB/IL-339

An alternative expression plasmid was constructed to facilitate efficient transfer of potentially interesting mutants into Bacillus expression vectors (see below). For this purpose, pGB/IL-336 was digested with HpaI and HindIII to remove most of the 3'-terminal part of the IL-3 cDNA. The protruding ends were made blunt and subsequently a blunt fragment carrying the corresponding IL-3 sequences (nt 137–497) and the *B. licheniformis* alpha-amylase terminator from plasmid pGB/IL-337 was ligated into it, resulting in plasmid pGB/IL-338. pGB/IL-337 had been constructed from pGB/IL-324 (as disclosed in EPA 0390252 which is incorporated herein by reference) by looping-out of 3' non-coding IL-3 cDNA and alpha-amylase structural sequences between the IL-3 stop codon in the cDNA and the alpha-amylase terminator, using a synthetic oligonucleotide (Table 1, 944). This oligonucleotide also introduced a XhoI site just downstream of the IL-3 stop codon. Plasmid pGB/IL-338 was digested with DamHI and HincII and part of the polylinker and 5'-terminal IL-3 sequences were substituted by the phosphorylated synthetic oligonucleotides 1055/1056 (Table 1) giving rise to plasmid pGB/IL-339. Thus, the IL-3 gene was reconstructed with a slightly modified heterologous signal peptide encoding sequence. A fusion protein of 148 aa with a calculated mw of 16,541 dalton was synthesized (FIG. 2). The DNA sequence of pGB/IL-339 was verified and found to be correct. The biological activity of the expressed fusion protein was found to be unaltered.

Another *E. coli* expression vector, pGB/IL-340, was constructed, in which the lacZ promoter is followed immediately by sequences encoding the Bacillus α-amylase signal peptide precisely fused to mature IL-3, with the amylase terminator downstream thereof. This plasmid, which also serves as an intermediate for the construction of Bacillus expression vectors, was constructed by introduction of the NdeI-KpnI fragment from pGB/IL-337, carrying all the sequences just mentioned, into the NdeI-KpnI-cleaved *E. coli* vector pTZ18RN. pTZ18RN is pTZ18R (Pharmacia) modified just upstream of the lacZ ATG start codon to introduce an NdeI site, using oligonucleotide 731 (see Table 1). pGB/IL-340 gives rise to high production of IL-3 in *E. coli*.

EXAMPLE 2

Construction of Deletion and Substitution Mutants

In vitro mutagenesis was performed using synthetic oligonucleotides (Table 1 and Table 2) according to the procedure developed by Kunkel et al. (1987) Meth. Enzymol. 154:367–382. Single-stranded template DNA was prepared by transformation of pGB/IL-336 or pGB/IL-339 DNA into *E. coli* strain CJ236 (BioRad) and superinfecton with M13K07 (Pharmacia) helper phage. Phage DNA was prepared according to standard procedures and fractionated on 0.6% low-melting agarose to remove the helper phage ssDNA. The excised band was melted and extracted with phenol. pGB/IL-336 or pGB/IL-339 ssDNA was recovered by butanol concentration and ethanol precipitation and tested for primer-dependent DNA synthesis in a sequencing reaction.

Purified pGB/IL-336 or pGB/IL-339 ssDNA (±100 ng) was annealed with 20 ng of phosphorylated primer at 65° C. and slowly cooled to room temperature. Synthesis of the complementary strand was performed using 1–2 μg of gene 32 protein, 4 units of T4-DNA polymerase and 2.5 units of T4-DNA ligase. Reaction was carried out at 0° C. for 5 min, at 20° C. for 10 min and at 37° C. for 90 min. After completion, one third of the reaction mixture was mixed with thawed competent (Hanahan, D. (1985) in: "DNA Cloning" (D. M. Glover ed.) Vol. 1, IRL Press, Washington) JM109 cells and plated. Individually picked colonies were used to inoculate liquid media and the cells were superinfected with the M13K07 helper phage to produce ssDNA. The sequence of the clones was verified using the M13 reverse sequencing primer and two IL-3 sequence specific primers (Table 1; 823: nt 118–137 and 824: nt 261–280).

The double cysteine mutant (9045) was constructed by ligation of the corresponding BstBI/BamHI fragments of the plasmids carrying the mutant IL-3 genes 904 and 905. Similarly, the combination mutants X and Z were constructed by ligation of fragments containing a 5' deletion and fragments containing a 3' deletion. Resulting clones were controlled by restriction enzyme analysis and sequence analysis.

Mutant 9329 was derived from 939 following HpaI and BamHI digestion and ligation with oligonucleotides 1424/1425. Clones were verified first for loss of the HpaI site and subsequently for correct DNA sequence.

From all transformants, plasmid DNA was isolated for a second round of transformation into JM109 cells to exclude potential contamination with the parental IL-3 construct. Following sequence verification, these clones were used for protein production.

Some of the mutants described here (811, 933 and 9329) were introduced into pGB/IL-340. This was done by ligating the PstI-XhoI fragment of a pGB/IL-339 derived mutant into PstI-XhoI cleaved pGB/IL-340, this resulted in plasmids pGB/IL-340/811, pGB/IL-340/933 and pGB/IL-340/9329.

Bacillus expression vectors for IL-3 muteins were constructed by exchanging the PstI-HindIII fragment of pGB/IL-322 (carrying part of the alpha-amylase signal peptide, the complete mature IL-3 cDNA sequence and the amylase terminator) with the PstI-HindIII fragment of a pGB/IL-340 mutant derivative (carrying part of the α-amylase signal peptide, the mutant IL-3 cDNA sequence and the α-amylase terminator). The Bacillus expression vectors for the muteins 811, 933 and 9329 were named pGB/IL-322/811, pGB/IL-322/933 and pGB/IL-322/9329, respectively.

Another mutant (1455 lacking amino acids 130–133) was constructed directly in pGB/IL-340 by loop-out mutagenesis, using oligonucleotide 1455 (Table 1), resulting in plasmid pGB/IL-340/1455. Subsequently, the mutant sequence was transferred to pGB/IL-322 in a similar way as described for mutants 811, 933 and 9329, resulting in plasmid pGB/IL-341.

TABLE 1

Mutagenesis Oligonucleotides

| Code | Sequence (5' → 3') | | Amino Acids Involved |
|---|---|---|---|
| 810 | AACTGCTCTAACATGCCTTTGCCTTTGCTG | SEQ ID NO:1 | 20–30 |
| 811 | CACTTAAAGCAGCCAGAAAATAACCTTCGA | SEQ ID NO:2 | 31–49 |

TABLE 1-continued

Mutagenesis Oligonucleotides

| Code | Sequence (5' → 3') | | Amino Acids Involved |
|---|---|---|---|
| | ‥ | | |
| 812 | ATGGAAAATAACCTTAACAGGGCTGTCAAG | SEQ ID NO:3 | 54–61 |
| | ‥ | | |
| 813 | TTCAACAGGGCTGTCCTCCTGCCATGTCTG | SEQ ID NO:4 | 66–80 |
| | ‥ | | |
| 820 | AATCTCCTGCCATGTGCACCCACGCGACAT | SEQ ID NO:5 | 85–90 |
| | ‥ | | |
| 821 | ACGGCCGCACCCACGGACTGGAATGAATTC | SEQ ID NO:6 | 94–102 |
| | ‥ | | |
| 822 | GGTGACTGGAATGAAAATGCGCAGGCTCAA | SEQ ID NO:7 | 107–119 |
| | ****** | | |
| 904 | GACAAGCTGGGTTAACGCTAGCAACATGATCGATGAA | SEQ ID NO:8 | Ala 16 |
| | **** | | |
| 905 | CTTAAAAATCTCCTGCCGGCGCTGCCCCTGGCCACGG | SEQ ID NO:9 | Ala 84 |
| | ‥ | | |
| 932 | CGGGGATCCGTCGACAACTGCTCTAACATG | SEQ ID NO:10 | 1–14 |
| | ‥ | | |
| 933 | ATAACACACTTAAAGAACAACCTCAATGGG | SEQ ID NO:11 | 29–37 |
| | ‥ | | |
| 934 | GGGGAAGACCAAGACAGGCCAAACCTGGAG | SEQ ID NO:12 | 47–54 |
| | ‥ | | |
| 935 | AGGCCAAACCTGGAGGCATCAGCAATTGAG | SEQ ID NO:13 | 60–70 |
| | ‥ | | |
| 936 | GCATCAGCAATTGAGTGTCTGCCCCTGGCC | SEQ ID NO:14 | 76–83 |
| | ‥ | | |
| 937 | TGTCTGCCCCTGGCCCCAATCCATATCAAG | SEQ ID NO:15 | 89–95 |
| | ‥ | | |
| 938 | CATATCAAGGACGGTACGTTCTATCTGAAA | SEQ ID NO:16 | 103–111 |
| | ‥ | | |
| 939 | CTGAAAACCCTTGAGGCGATCTTTTGAGTC | SEQ ID NO:17 | 120–130 |
| 823 | CCTTGAAGACAAGCTGGGTT | SEQ ID NO:18 | |
| 824 | CCAAACCTGGAGGCATTCAA | SEQ ID NO:19 | |
| 419 | TCGACGCTCCCATGACCCAGACAACGCCCTTGAAGACAAGCTGGGTT | SEQ ID NO:20 | |
| 420 | AACCCAGCTTGTCTTCAAGGGCGTTGTCTGGGTCATGGGAGCG | SEQ ID NO:21 | |
| 731 | CAGGAAACACATATGACCATGATT | SEQ ID NO:22 | |
| 944 | TGAGCCTCGCGATCTTTTGACTCGAGTAGAAGAGCAGAGAGGACGG | SEQ ID NO:23 | |
| 1055 | GATCCTCTGCAGCAGCGGCGGCTCCCATGACCCAGACAACGCCCTTGAAGACAAGCTGGGTT SEQ ID NO:24 | | |
| 1056 | AACCCAGCTTGTCTTCAAGGGCGTTGTCTGGGTCATGGGAGCCGCCGCTGACAAGCTGGGTT SEQ ID NO:25 | | |
| 1424 | GATCCTCTGCAGCAGCGGCG | SEQ ID NO:26 | |
| 1425 | CGCCGCTGCTGCAGAG | SEQ ID NO:27 | |
| 1455 | CTCAACAGACGACTTTGAGCTGACTCGAGTAGAAGAGCAGAG | SEQ ID NO:28 | |

. indicates nucleotide next to the deletion in the IL-3 gene.
* indicates nucleotide substitutions in the IL-3 sequence.

TABLE 2

Oligonucleotides for Substitution Mutagenesis

| Code | Sequence (5' → 3') | | Amino Acids Involved |
|---|---|---|---|
| 904 | GACAAGCTGGGTTAACGCTAGCAACATGATCGATGAA | SEQ ID NO:29 | 16 |
| 905 | CTTAAAAATCTCCTGCCGGCGCTGCCCCTGGCCACGG | SEQ ID NO:30 | 84 |
| 1480 | TTGCCTTTGCTGCGCTTCAACAACCTC | SEQ ID NO:31 | 36 |
| 1481 | AACCTCAATGGGAAACGCCAAGACATTCTG | SEQ ID NO:32 | 43–44 |
| 1482 | GGGGAAGACCAACGCATTCTGATGAA | SEQ ID NO:33 | 46 |
| 1483 | GACATTCTGATGAAAAATAACCTTCGA | SEQ ID NO:34 | 50 |
| 1484 | GAAAATAACCTTGAAGATCCAAACCTGGAG | SEQ ID NO:35 | 54–55 |
| 1485 | AGGCCAAACCTGAAAGCATTCAACAGG | SEQ ID NO:36 | 59 |
| 1486 | GAGGCATTCAACCCGGGCGTCAAGAGTTTA | SEQ ID NO:37 | 63–64 |
| 1487 | GCATCAGCAATT[C/G]GTAGCATTCTTAAA | SEQ ID NO:38 | 75 |
| 1488 | GAGAGCATTCTTGAAAATCCTGCCA | SEQ ID NO:39 | 79 |
| 1489 | GCCGCACCCACGCCGCATCCAATCCAT | SEQ ID NO:40 | 94 |
| 1490 | CGACATCCAATCGAAATCGATCAGGGTGACTGGAAT | SEQ ID NO:41 | 98–101 |
| 1491 | GGTGACTGGAATAAATTCCCGGAGGAAA | SEQ ID NO:42 | 106 |
| 1492 | TGGAATGAATTCGAAGATGAACTGACGTTCTAT | SEQ ID NO:43 | 108–110 |
| 1493 | AGGAAACTGACGGCGACCCTGAAAACCCTT | SEQ ID NO:44 | 113–114 |

EXAMPLE 3

Purification of IL-3 Muteins from

E. coli and B. licheniformis

E. coli JM109 cultures (100 ml) were inoculated with 0.5 ml of a fresh overnight culture of the (mutant) IL-3 clone and grown at 37° C. until an OD of 0.4–0.6 at 550 nm was reached. Plasmid-directed protein synthesis was induced by addition of 1 mM of IPTG (Pharmacia). After an additional culture for 3–16 hours, the cells were collected by centrifugation (10 min, 4000 rpm at 4° C.) and stored frozen.

The bacteria were suspended in 10 ml of TE (10 mM Tris-HCl pH 8; 1 mM EDTA) and lysozyme was added (0.025%=500 µg/ml). Following incubation for 30 min at room temperature, $MgCl_2$ and DNase were added to final concentrations of 10 mM and 20 µg/ml, respectively. After incubation at 37° C. for 15 min, Tween 20 (0.2%), DTT (2 mM) and PMSF (0.1 mM) were added. The suspension was cooled on ice and vigorously sonified (two times, 35 sec.). The homogenate was clarified by centrifugation (30 min. 15,000×g, 10,000 rpm in a Beckman JS13.1 rotor) at 4° C. and the supernatant was discarded.

The pellet was resuspended in 4 ml of 55% sucrose in buffer TPD (50 mM Tris-HCl, pH 8; 0.1 mM PMSF and 2 mM DTT) by sonification and layered onto a discontinuous sucrose gradient (2 ml portions of 75% and 60% of sucrose in TPD buffer), essentially as described in WO 88/00598. Following centrifugation at 200,000×g (35,000 rpm in a Sorvall TH641 rotor) at 25° C. for 2 hours, the inclusion bodies containing the IL-3 proteins were recovered from the 75% sucrose interphase.

After at least 4-fold dilution, the inclusion bodies were pelleted at 25,000×g (30 min at 13,000 rpm in the Beckman JS13.1 rotor) and sonificated in 5 ml of 8 M urea containing 50 mM Tris-HCl pH 8.9 and 2 mM DTT and left overnight at 4° C. The clarified solution was subsequently applied to a 3 ml DEAE-Sepharose Fast Flow column (Pharmacia), equilibrated with 8 M urea, 50 mM Tris-HCl pH 8.9 and 1 mM DTT buffer. The IL-3 protein was bound to the column and step eluted with 75 mM NaCl in the same buffer. The eluted protein was dialyzed against several portions of 10 mM Tris-HCl pH 8.0 and 1 mM DTT buffer and made isotonic by adding 10-fold concentrated RPMI cell culture medium (Sigma) containing 1% bovine serum albumin. The filter sterilized (0.22 µm Millex-GV, Millipore) solution was used for biochemical and biological characterization.

Mutant proteins 811, 933, 1455 and 9329, X and Z, produced by Bacillus were secreted into the culture medium and did not require such drastic purification procedures for testing of biological activity. Therefore, the clarified supernatant (1 liter) (adjusted to 5 mM EDTA, 1 mM PMSF and 1 M ammonium sulfate) was passed over a 15–20 ml Fractogel TSK Butyl 650 (C) column (Merck) equilibrated with 1 M ammonium sulfate in 10 mM Tris-HCl pH 7.0 buffer. The bound IL-3 protein was eluted with 10 mM Tris-HCl buffer and subsequently passed over a 1.5 ml DEAE-Sepharose Fast Flow column equilibrated with 10 mM Tris-HCl pH 8.0 buffer. The flow-through was collected and adjusted to 70% ammonium sulfate to concentrate the IL-3 protein. The precipitate was collected by centrifugation at 10,000 rpm (JS-13 rotor), dissolved and dialyzed against 10 mM Tris-HCl pH 8.0, 1 mM DTT buffer.

Samples corresponding to 25–100 µl of the original bacterial culture were analyzed on 0.75×75×100 mm (BioRad miniprotean II) 13.5% SDS-polyacrylamide gels (acryl/bisacryl=29/1). Proteins were visualized by either Coomassie Brilliant Blue G250 staining or immunological methods. FIG. 3 shows an example of purified muteins expressed in E. coli.

The expression in E. coli of mutant pGB/IL-339 derived IL-3 proteins was generally higher than the same mutant protein from the pGB/IL-336 expression vector. The applied purification procedure was not devised to render completely pure IL-3 protein preparations. In general, minor higher molecular weight contaminants were observed on SDS gels. Using densitometric scanning of stained SDS gels, the amount of IL-3 protein was determined. Although occasionally severe loss of protein occurred following dialysis, total recovery was generally 0.1–1 mg of "purified" IL-3 protein. The only exception were the mutants 811 and 933, which gave no fusion protein production in either of the E. coli expression vectors. Northern analysis indicated a strong reduction of IL-3 specific RNA in the bacteria, whereas no significant difference in the plasmid DNA content was observed. This result suggests that probably mRNA stability is decreased through the deletions introduced in the eukaryotic IL-3 cDNA sequence.

The only convenient method for synthesis of the muteins 811 and 933 is expression in Bacillus licheniformis. Although the amount of protein produced is very low compared to the amount of protein produced by Bacillus strains synthesizing other muteins such as 9329 and 1455, enough is made to purify the muteins 811 and 933 in sufficient quantities to carry out the biological assays described herein.

EXAMPLE 4

Immunological Characterization of the IL-3 Muteins

Preparation of polyclonal and monoclonal antisera has been described in WO 88/04691.

For immunological detection of IL-3 muteins, the gel fractionated proteins (see Example 3) were transferred onto nitrocellulose (0.2 µm, Schleicher and Schuell BA83) using the semi-dry blotting system (Novablot, Pharmacia/LKB) with a continuous buffer system (39 mM glycine, 48 mM Tris, 0.0375% SDS and 20% methanol) at 1.2 mA/cm$^2$ for 90 min. The nitrocellulose filter was subsequently air dried, preincubated with a 3% bovine serum albumin (BSA, Sigma) solution (10 mM Tris-HCl pH 7.6; 350 mM NaCl; 0.1% PMSF and 0.1% sodium azide) and incubated for 4–16 hr with the polyclonal ($10^{-3}$ dilution) or a mixture of monoclonal antibodies directed against human IL-3 (MCA A1, A4, A5, A8, A18 at $10^{-4}$ dilution) in RIA buffer (10 mM Tris/HCl, pH 7.6; 150 mM NaCl; 1% Triton X-100; 0.1% SDS; 0.5% Na-deoxycholate; 0.1 mM PMSF and 0.3% BSA). Immunological complexes were visualized using biotinylated anti-rabbit or mouse Ig, streptavidin-biotinylated horseradish peroxidase (Amersham International, Amersham, UK) and 4-chloro-1-naphtol (Gibco-BRL) according to the protocols provided by the manufacturer.

Alternatively, antiserum incubations were performed in Tris-buffered saline plus 0.05% Tween 20. Alkaline phosphatase-linked anti-mouse Ig complexes were visualized according to standard protocols (Promega).

The data, pertaining to the interaction of specific monoclonal antibodies with hIL-3 muteins in western blotting experiments, are presented in Table 3.

TABLE 3

Evaluation of IL-3/MCA Data

| MUTANT (AA) | 4810 20–30 | 933 29–37 | 811 31–49 | 934 47–54 | 812 54–61 | 935 60–70 | 4813 66–80 | ALL OTHER | 36D→R 1480 | 43ED→KR 1481 | 46D→R 1482 |
|---|---|---|---|---|---|---|---|---|---|---|---|
| MCA | | | | | | | | | | | |
| A1  | ++ | -- | -- | ++ | ++ | ++ | ++ | ++ | ++ | ++ | ++ |
| A4  | ++ | ++ | ++ | ++ | +  | +  | +  | ++ | ++ | ++ | ++ |
| A5  | ++ | ++ | -- | -- | +  | ++ | ++ | ++ | ++ | ++ | -- |
| A8  | ++ | ++ | -- | ++ | ++ | ++ | ++ | ++ | ++ | -- | +  |
| A18 | ++ | -- | -- | ++ | ++ | ++ | ++ | ++ | +  | ++ | ++ |
| 2   | ++ | -- | -- | ++ | ++ | ++ | ++ | ++ | | | |
| 3   | ++ | ++ | -- | -- | +  | ++ | ++ | ++ | | | |
| 6   | ++ | ++ | -- | +  | ++ | ++ | ++ | ++ | | | |
| 10  | ++ | ++ | -- | +  | ++ | ++ | ++ | ++ | | | |
| 12  | ++ | -- | -- | ++ | ++ | ++ | ++ | ++ | | | |
| 13  | +  | -- | -- | ++ | ++ | +  | +  | ++ | | | |
| 14  | ++ | ++ | -- | -- | +  | ++ | ++ | ++ | | | |
| 15  | ++ | -- | -- | ++ | ++ | ++ | ++ | ++ | | | |
| 26  | ++ | ++ | -- | +  | ++ | ++ | ++ | ++ | | | |
| 27  | ++ | ++ | ++ | ++ | +  | +  | +  | ++ | | | |
| 32  | ++ | -- | -- | ++ | ++ | ++ | ++ | ++ | | | |
| 33  | ++ | -- | -- | ++ | ++ | ++ | ++ | ++ | | | |

A: ascites monoclonals
++: full response on western blot
+: at least 5-fold reduced response
--: no reaction observed From a review of Table 3, it is apparent that the majority of the monoclonal antibodies raised against the gel-purified denatured fusion protein are directed against epitopes located between residues 30 and 50 of the mature IL-3 polypeptide. These epitopes mostly reflect linear polypeptide chains, only one example (13) of a discontinuous epitope has been identified. The largest group is capable of identifying the 933 mutant, but fails to react with t he 811 mutant. Thus, the epitope must reside between residues 37 and 50. This region is highly hydrophilic with a postulated β-turn and α-helix (DNASIS software) and was proposed to be an antigenic determinant using Hopp and Wood algorithm. The second group of antibodies is characterized by the absence of reaction with mutant 933 (which lacks 9 amino acids). This hydrophobic, proline-rich coil region is not predicted to be a major antigenic site.

More refined localization of these epitopes comes from reaction of the ascites monoclonals with the following substitution mutants: $Asp^{36} \rightarrow Arg$, $Glu^{43}Asp \rightarrow Lys^{43}Arg$ and $Asp^{46} \rightarrow Arg$.

Further characterization of the ascites monoclonals by double sandwich ELISA revealed lack of interference between A1 and A5 or A8, and between A5 and A18. Competition ELISA showed cross-competition between A1 and A18, between A5 and A8, and between A8 and A18. No cross-competition was observed with A4. These data are in agreement with the immunoblotting experiments. Furthermore, ascites antibodies were found to react with hIL-3 preparations from mammalian, bacterial and yeast cultures, irrespective of glycosylation state.

From the combined information of these immunological tests epitopes can be localized as follows:

A1 and A18 are aimed against an epitope localized between amino acids 29 and 37. Furthermore, from the 36 D→R mutant it can be concluded that the A18 epitope is localized somewhat more toward the C-terminus than the A1 epitope.

A5 is aimed against an epitope localized between amino acids 45 and 54.

A8 is aimed against an epitope localized between amino acids 36 and 47.

EXAMPLE 5

Biological Characterization of the IL-3 Muteins
A. AML DNA Synthesis

AML DNA synthesis was tested on human AML193 cells as follows. Human AML193 cells (ATCC: CRL-9589) were maintained in Serum Free Medium (SFM), (Iscove's Modified Dulbecco's Medium (Gibco BRL) containing 0.1% BSA (Behringwerke AG, Marburg), 10 µg/ml of Insulin (Organon) and Transferrin, 0.1 mM beta-mercaptoethanol) and 10 to 20 units of human IL-3.

Dilutions of (mutant) IL-3 preparations were prepared (50 µl) in round bottom 96 well plates in SFM. Washed cells ($1-2\times10^4$ in 50 µl SFM) were added and cultured for 6 days. $^3$H-Thymidine (0.1 uCi, 2 uCI/mmol) was added in 20 µl and cells were harvested 16 hours later. A unit of IL-3 activity was defined as the amount required to give 50% of maximal DNA synthesis in this assay. For the reference IL-3 preparation, the specific activity varied between $2\times10^6$ to $2\times10^7$ Units per mg protein. In general, the biological activity of the muteins was compared to this reference preparation.

Figure 4:
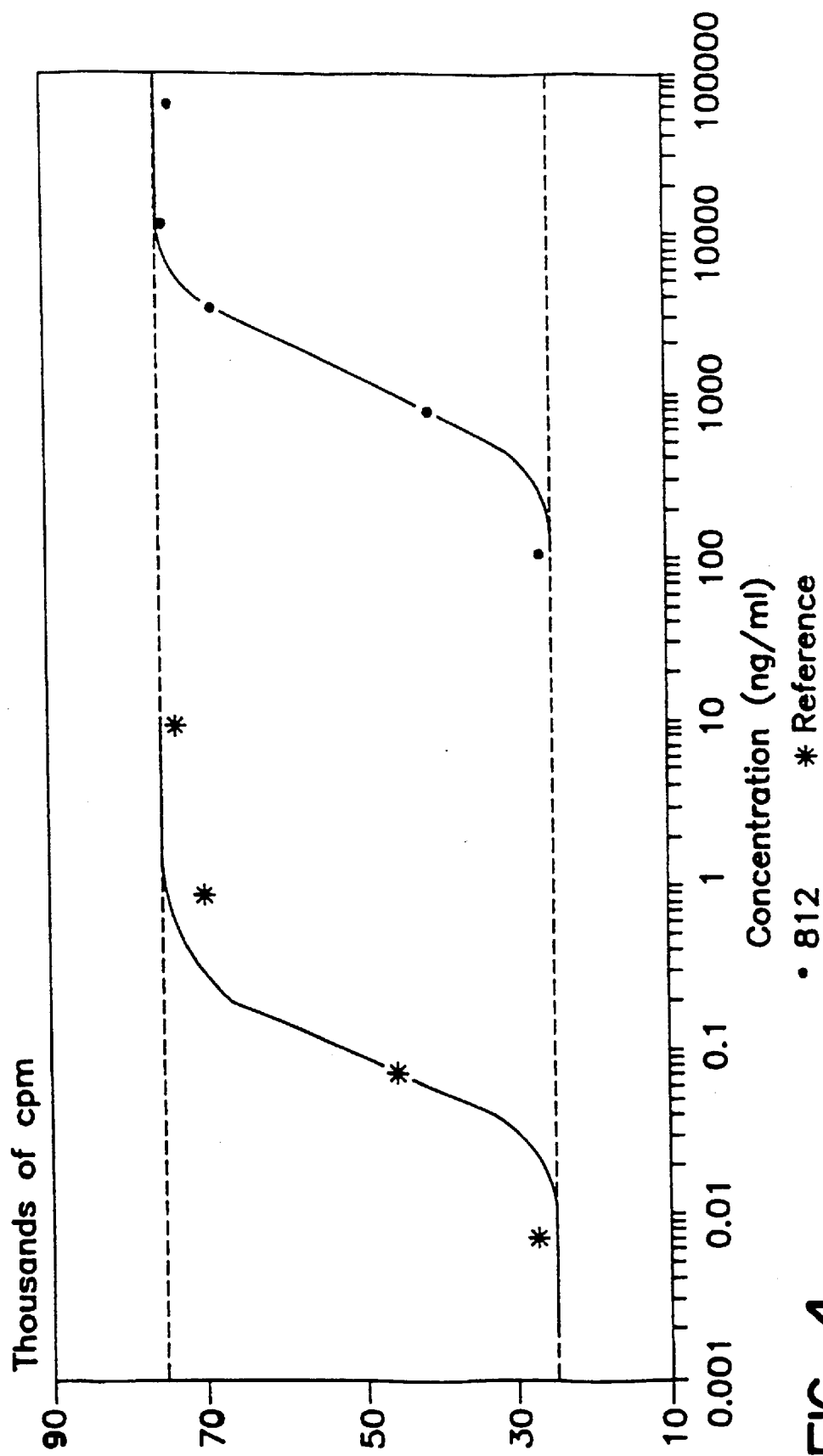
FIG. 4 shows an AML proliferation assay for IL-3 (*) and IL-3 mutant 821 (˙).

FIG. 4 shows an example of the AML proliferation assay in which mutein 812 is compared with the reference IL-3 expressed in Bacillus. The graph shows that the mutein 812 has an activity which is reduced by about 4 orders of magnitude with respect to unmodified IL-3. However, the mutein is still able to stimulate the AML cells to maximal activity, only more protein is needed.

B. IL-3 Receptor Assay

Figure 5:
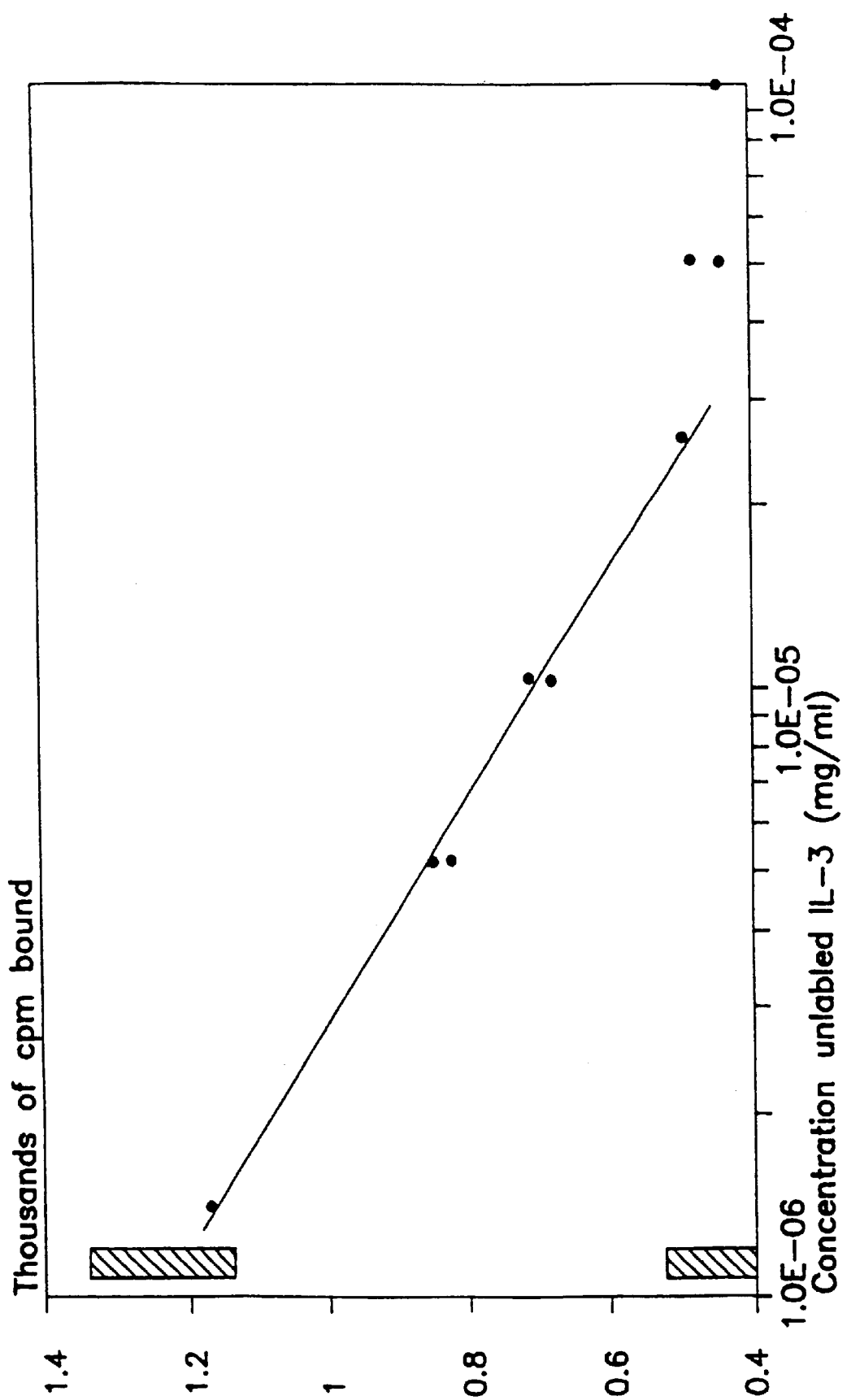
FIG. 5 shows an IL-3-receptor binding experiment. Radiolabeled IL-3 binding to patient AML blasts is competed with unlabeled IL-3 protein (reference preparation). The levels of non-specific (lower bar) and maximal total binding (upper bar) in this experiment are indicated (see Example 5).

An ILK3 receptor binding assay was performed with purified recombinant hIL-3 (see EPA 0390252) was radiolabeled with the Bolton-Hunter reagent (as described by Budel et al., Blood 74 (1989) 565–571). The specific activity was estimated at 80,000 cpm/ng of IL-3. As target, either donor leukocytes, patient AML cells, or MV4-11 (ATCC: CRL-9591) cells were used. Cells were washed in Hanks Balanced Salt solution and suspended in Alpha-MEM plus 1% BSA. Usually, 3–10×10⁶ cells were incubated with 200–300 pM of radiolabeled IL-3 and various concentrations of unlabeled mutant protein in a total volume of 200 µl for 1 hr at 37° C. Cell-bound labeled IL-3 was centrifuged for 10 min at 1000×g at 4° C. through a 0.5 ml cushion of bovine calf serum in an Eppendorf tube (Budel et al., 1989). The tubes were frozen in liquid nitrogen and the tips cut off for counting in a Packard gamma counter. Competition binding was determined relative to the reference preparation. FIG. 5 shows an example of an IL-3 receptor binding experiment. Radiolabeled IL-3 binding to patient AML blasts is competed with unlabeled IL-3 protein (reference preparation). Due to the low number of receptors (less than 200) on the target cells, data for competition mostly varied by one order of magnitude.

Figure 6:
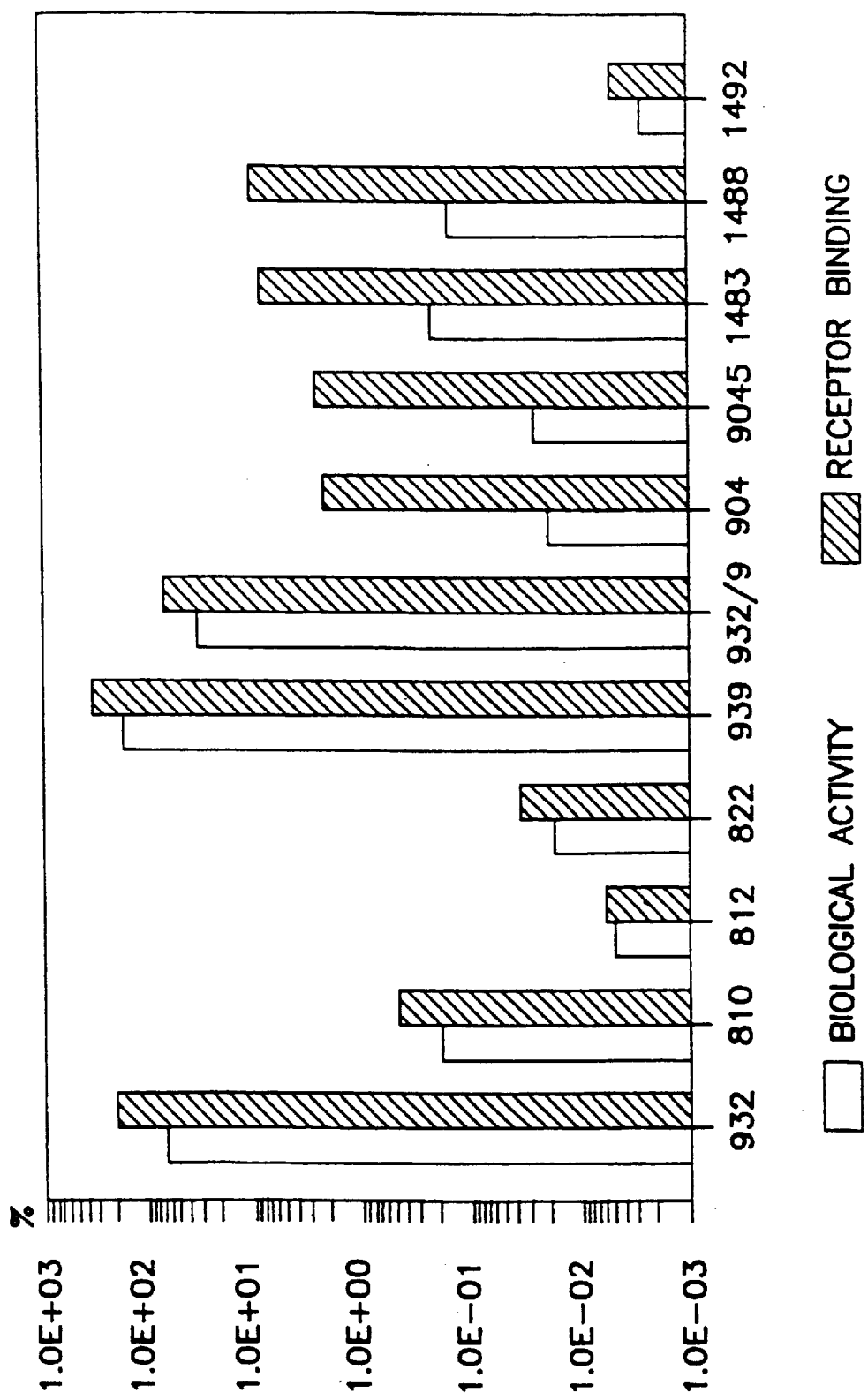
FIG. 6 shows a comparison of selected mutant IL-3 proteins with respect to relative biological activity (open bars) and relative binding activity (closed bars). The percentage of activity compared to the reference IL-3 preparation is indicated (Table 4).

The results from the above assays are presented in Table 4. The biological activity of the deletion mutants and the Cys→Ala substitution mutants is graphically presented in FIG. 6.

As can be seen, IL-3 fusion proteins derived from both pGB/IL-336 and pGB/IL-339 expression plasmids were identical in biological activity and were not significantly different from the *B. licheniformis* reference preparation derived from expression of the full-length IL-3 cDNA in pGB/IL-322 (see EPA 0390252). Apparently, no negative effect on the biological activity is exerted by the heterologous leader peptide in the *E. coli* fusion proteins. Most IL-3 deletion mutants were significantly reduced in biological activity. Deletions between amino acids 50 and 105 resulted in more than 10,000-fold reduction in specific activity. However, in all cases, residual biological activity was detected, indicating the sensitivity of the bio-assay and the absence of toxic components in the protein preparations. Complete recovery of biological activity was observed for deletion mutants 932 (1–14) and 939 (120–130) and the corresponding double mutant 9329 as well as for the C-terminal mutant 1455. The deleted N- and C-terminal sequences are apparently not involved in binding to the receptor or proper folding of the molecule. In contrast, single substitutions of the cysteine residues (mutants 904 and 905) resulted in a 5,000-fold reduction of biological activity. Similar effects were seen with a double cysteine mutant (9045), indicating that the S-S bridge plays an important stabilizing role in the native IL-3 molecule.

The muteins expressed in *E. coli* described above are all fusion proteins. To provide evidence that the extra N-terminal amino acids are not necessary as compensation for the loss of the deleted IL-3 specific amino acids, construct pGB/IL-322/9329 was made and expressed in *B. licheniformis*. This construct gives rise to a 1–14/120–130 IL-3 mutein without any extra amino acids at the N-terminus. The activity of this mutein is comparable to the wild-type molecule proving that only the residual 108 amino acids are responsible for the IL-3 activity.

Receptor binding of most of the mutant IL-3 proteins was determined. The binding experiments do not allow for detailed comparison of receptor binding activity due to the low receptor numbers on the target cells. However, in general there is a good correlation between biological activity and receptor binding (Table 4). For most mutant IL-3 proteins, the ratio between relative binding and biological activity is approximately 1. The muteins 1483, 488, 904 and 9045 show considerably higher ratios (Table 4 and FIG. 6), indicating potential antagonistic activity. This means that these molecules can be regarded as partial antagonists of IL-3. Upon further experimentation, muteins may be found that have the same binding capacity as native IL-3 but that has a 10⁴-fold lower activity. Those molecules would be true antagonists of IL-3. The approach described in this invention provides the means and methods to obtain such molecules.

TABLE 4

Biological Activities of IL-3 Mutants

| MUTANT CODE | AMINO ACID DELETION OR SUBSTITUTION[1] | REL. SPEC. BIOLOGICAL ACTIVITY[2] | RELATIVE ANTAGONISTIC POTENTIAL[3] |
|---|---|---|---|
| Ref. | | 1.0 | |
| pGB/IL-339 | | $3.7 \times 10^{-1}$ | |
| pGB/IL-336 | | $7.9 \times 10^{-1}$ | 1.1 (0.2–3.3) |
| 932 | 1–14 | $7.1 \times 10^{-1}$ | 2.8 (0.6–4.9) |
| 810 | 20–30 | $2.1 \times 10^{-3}$ | 2.4 |
| 934 | 47–54 | $7.3 \times 10^{-5}$ | N.C. |
| 812 | 54–61 | $5.3 \times 10^{-5}$ | 1.2 (0.9–1.4) |
| 935 | 60–70 | $1.2 \times 10^{-5}$ | N.C. |
| 813 | 66–80 | $2.4 \times 10^{-5}$ | N.C. |
| 936 | 76–83 | $6.4 \times 10^{-6}$ | N.C. |
| 820 | 85–90 | $1.1 \times 10^{-5}$ | N.C. |
| 937 | 89–95 | $1.0 \times 10^{-5}$ | N.C. |
| 821 | 94–102 | $1.8 \times 10^{-5}$ | N.C. |
| 938 | 103–111 | $6.6 \times 10^{-5}$ | N.C. |
| 822 | 107–119 | $2.1 \times 10^{-4}$ | 1.9 (0.6–3.9) |
| 939 | 120–130 | 2.0 | 1.8 (0.3–2.8) |
| 9329 | 1–14/120–130 | $4.0 \times 10^{-1}$ | 2.0 (1.8–2.1) |
| 904 | 16C → A | $2.4 \times 10^{-4}$ | 100 (33–210) |
| 905 | 84C → A | $1.9 \times 10^{-4}$ | 11 (4.8–38) |
| 9045 | 16/84C → A | $3.1 \times 10^{-4}$ | 88 (13–170) |
| 1480* | 36D → R | $3.1 \times 10^{-3}$ | 12 |
| 1481 | 43ED → KR | $<1.5 \times 10^{-4}$ | N.C. |
| 1482* | 46D → R | $7.5 \times 10^{-3}$ | 0.6 |
| 1483 | 50E → K | $2.7 \times 10^{-3}$ | 37 (4–67) |
| 1484 | 54RR → ED | $8.0 \times 10^{-5}$ | 3.5 (2.3–4.7) |
| 1485* | 59E → K | $1.1 \times 10^{-2}$ | 3 |
| 1486 | 63RA → PG | $9.8 \times 10^{-5}$ | 14 (3.5–27) |
| 1487A* | 75E → G | $1.5 \times 10^{-2}$ | 3 |
| 1487B* | 75E → R | $8.6 \times 10^{-3}$ | 3 |
| 1488 | 79K → E | $1.9 \times 10^{-3}$ | 65 (54–77) |
| 1489 | 94R → P | $1.7 \times 10^{-3}$† | N.C. |
| 1490* | 98HIKD → EIKQ | $2.2 \times 10^{-3}$ | 5 |
| 1491* | 106E → K | $3.2 \times 10^{-4}$ | 6 |
| 1492 | 108RRK → EDE | $3.1 \times 10^{-5}$ | 2 (1.2–3) |
| 1493 | 113FY → AT | $<1.2 \times 10^{-5}$ | N.C. |
| X¤ | 1–14/120–133 | $2.3 \times 10^{-1}$ | 8.9 (3.6–14) |
| Z¤ | 1/14/116–133 | $1.1 \times 10^{-1}$† | 1.6 (1–1.9) |
| 933¤ | 29–37 | $5.7 \times 10^{-3}$† | 1.1 (0.2–2.9) |
| 811¤ | 31–49 | $4.8 \times 10^{-3}$† | 1.6 (0.5–3.2) |

[1]Deletion between amino acid numbers of mature human IL-3 is indicated. Substitutions of amino acids are indicated in single letter code.
[2]Median specific biological activity is expressed relative to the reference IL-3 preparations.
[3]Antagonistic potential is represented as relative receptor binding activity divided by relative biological activity. The range is presented between brackets.
NC No competition was observed for the particular mutein preparation.
*Inclusion bodies were pelleted from sucrose solutions and solubilized in urea. Muteins were diluted in medium and tested for biological activity. Receptor binding experiments were performed once.
†Mutein protein concentration was too low for densitometric scanning and was estimated from gels and western blots.
¤Mutant proteins were expressed in Bacillus and lack a leader polypeptide sequence.

All publications (including patents and patent applications) mentioned in this specification are indicative to the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be apparent to one of ordinary skill in the art that many changes and modifications can be made thereto without departing from the spirit or scope of the appended claims.

What is claimed is:

1. A human interleukin-3 antagonist having an amino acid sequence which differs from the sequence of human interleukin-3 by the replacement of one or both of $Cys^{16}$ or $Cys^{84}$ by another amino acid so as to disturb the disulfide bridge between $Cys^{16}$ or $Cys^{84}$.

2. The IL-3 antagonist of claim 1 which is a human IL-3 amino acid sequence selected from the group consisting of a polypeptide analog comprising a $Cys^{16} \rightarrow Ala^{16}$ substitution, a polypeptide analog comprising a $Cys^{84} \rightarrow Ala^{84}$ substitution, and a polypeptide analog comprising a $Cys^{16}Cys^{84} \rightarrow Ala^{16}Ala^{84}$ substitution.

3. A DNA molecule comprising a DNA sequence encoding an antagonist according to claim 1.

4. A vector comprising a DNA sequence encoding a polypeptide analog according to claim 1, in combination with transcription and translation regulation sequences that enable the expression of said polypeptide analog in a suitable host cell.

5. A host cell transformed with a vector according to claim 4.

6. A method to produce an antagonist of human interleukin-3 which differs from the amino acid sequence of human interleukin-3 by replacement of one or both of $Cys^{16}$ or $Cys^{84}$ by another amino acid so as to disturb the disulfide bridge between $Cys^{16}$ or $Cys^{84}$, which method comprises culturing cells according to claim 5 under conditions suitable for producing said antagonist; and recovering the antagonist from the culture.

7. A human interleukin-3 antagonist having an amino acid sequence which differs from the sequence of human interleukin-3 by a charge reversal substitution at one or more of positions 36, 50, and 79.

8. A DNA molecule comprising a DNA sequence encoding an antagonist according to claim 7.

9. A vector comprising a DNA sequence encoding an antagonist according to claim 7, in combination with transcription and translation regulation sequences that enable the expression of said antagonist within a suitable host cell.

10. A host cell transformed with a vector according to claim 9.

11. A method to produce an antagonist of human interleukin-3 which differs from the amino acid sequence of human interleukin-3 by a charge reversal substitution at one or more of positions 36, 50, and 79, which method comprises culturing cells according to claim 10 under conditions suitable for producing said antagonist; and recovering the antagonist from the culture.

12. The interleukin-3 antagonist of claim 7 having one or more charge reversal substitutions selected from the group consisting of $Asp^{36} \rightarrow Arg^{36}$, $Glu^{50} \rightarrow Lys^{50}$, and $Lys^{79} \rightarrow Glu^{79}$.

13. A human interleukin-3 antagonist having an amino acid sequence which differs from the sequence of human interleukin-3 by the substitutions $Arg^{63}Ala^{64} \rightarrow Pro^{63}Gly^{64}$.

14. A DNA molecule comprising a DNA sequence encoding an antagonist according to claim 13.

15. A vector comprising a DNA sequence encoding an antagonist according to claim 13, in combination with transcription and translation regulation sequences that enable the expression of said antagonist within a suitable host cell.

16. A host cell transformed with a vector according to claim 15.

17. A method to produce an antagonist of human interleukin-3 which differs from the amino acid sequence of human interleukin-3 by the substitutions $Arg^{63}Ala^{64} \rightarrow Pro^{63}Gly^{64}$, which method comprises culturing cells according to claim 16 under conditions suitable for producing said antagonist; and recovering the antagonist from the culture.

18. A method to produce a biologically active analog of human interleukin-3 wherein said analog differs from the amino acid sequence of human interleukin-3 by having deleted therefrom 4 to 18 amino acids from the C terminus of human interleukin-3, which method comprises culturing cells transformed with a vector, comprising a DNA sequence encoding a polypeptide analog of human interleukin-3 having the amino acid sequence of human interleukin-3 having deleted therefrom 4 to 18 amino acids from the C terminus of the native human interleukin-3 sequence, in combination with transcription and translation regulation sequences that enable the expression of said polypeptide analog, under conditions suitable for producing said analog; and recovering the analog from the culture.

\* \* \* \* \*

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:1:

AACTGCTCTA ACATGCCTTT GCCTTTGCTG                                30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:2:

CACTTAAAGC AGCCAGAAAA TAACCTTCGA                                30

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:3:

ATGGAAAATA ACCTTAACAG GGCTGTCAAG                                30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:4:

TTCAACAGGG CTGTCCTCCT GCCATGTCTG                                30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:5:

AATCTCCTGC CATGTGCACC CACGCGACAT                                30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single (D) TOPOLOGY: linear (xi) SEQUENCE DESCRIPTION: SEQ ID NO:6:

ACGGCCGCAC CCACGGACTG GAATGAATTC                                                30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:7:

GGTGACTGGA ATGAAAATGC GCAGGCTCAA                                                30

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:8:

GACAAGCTGG GTTAACGCTA GCAACATGAT CGATGAA                                        37

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:9:

CTTAAAAATC TCCTGCCGGC GCTGCCCCTG GCCACGG                                        37

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:10:

CGGGGATCCG TCGACAACTG CTCTAACATG                                                30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

ATAACACACT TAAAGAACAA CCTCAATGGG                                                30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:12:

GGGGAAGACC AAGACAGGCC AAACCTGGAG                30

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:13:

AGGCCAAACC TGGAGGCATC AGCAATTGAG                30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

GCATCAGCAA TTGAGTGTCT GCCCCTGGCC                30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:15:

TGTCTGCCCC TGGCCCCAAT CCATATCAAG                30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

CATATCAAGG ACGGTACGTT CTATCTGAAA                30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:17:

CTGAAAACCC TTGAGGCGAT CTTTTGAGTC                30

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

CCTTGAAGAC AAGCTGGGTT                                                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

CCAAACCTGG AGGCATTCAA                                                    20

(2) INFORMATION FOR SEQ ID NO:20:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:20:

TCGACGCTCC CATGACCCAG ACAACGCCCT TGAAGACAAG CTGGGTT                      47

(2) INFORMATION FOR SEQ ID NO:21:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:21:

AACCCAGCTT GTCTTCAAGG GCGTTGTCTG GGTCATGGGA GCG                          43

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:22:

CAGGAAACAC ATATGACCAT GATT                                               24

(2) INFORMATION FOR SEQ ID NO:23:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:23:

TGAGCCTCGC GATCTTTTGA CTCGAGTAGA AGAGCAGAGA GGACGG                       46

(2) INFORMATION FOR SEQ ID NO:24:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:24:

GATCCTCTGC AGCAGCGGCG GCTCCCATGA CCCAGACAAC GCCCTTGAAG ACAAGCTGGG    60

TT                                                                  62

(2) INFORMATION FOR SEQ ID NO:25:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:25:

AACCCAGCTT GTCTTCAAGG GCGTTGTCTG GGTCATGGGA GCCGCCGCTG CTGCAGAG      58

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

GATCCTCTGC AGCAGCGGCG                                               20

(2) INFORMATION FOR SEQ ID NO:27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:27:

CGCCGCTGCT GCAGAG                                                   16

(2) INFORMATION FOR SEQ ID NO:28:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:28:

CTCAACAGAC GACTTTGAGC TGACTCGAGT AGAAGAGCAG AG                       42

(2) INFORMATION FOR SEQ ID NO:29:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:29:

GACAAGCTGG GTTAACGCTA GCAACATGAT CGATGAA                            37

(2) INFORMATION FOR SEQ ID NO:30:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:30:

CTTAAAAATC TCCTGCCGGC GCTGCCCCTG GCCACGG                                37

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:31:

TTGCCTTTGC TGCGCTTCAA CAACCTC                                           27

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:32:

AACCTCAATG GGAAACGCCA AGACATTCTG                                        30

(2) INFORMATION FOR SEQ ID NO:33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:33:

GGGGAAGACC AACGCATTCT GATGGAA                                           27

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:34:

GACATTCTGA TGAAAATAA CCTTCGA                                            27

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:35:

GAAAATAACC TTGAAGATCC AAACCTGGAG                                        30

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:36:

AGGCCAAACC TGAAAGCATT CAACAGG                               27

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:37:

GAGGCATTCA ACCCGGGCGT CAAGAGTTTA                             30

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:38:

GCATCAGCAA TTSGTAGCAT TCTTAAA                                27

(2) INFORMATION FOR SEQ ID NO:39:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:39:

GAGAGCATTC TTGAAAATCT CCTGCCA                                27

(2) INFORMATION FOR SEQ ID NO:40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:40:

GCCGCACCCA CGCCGCATCC AATCCAT                                27

(2) INFORMATION FOR SEQ ID NO:41:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:41:

CGACATCCAA TCGAAATCGA TCAGGGTGAC TGGAAT                      36

(2) INFORMATION FOR SEQ ID NO:42:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:42:

-continued

```
GGTGACTGGA ATAAATTCCC GGAGGAAA                                              28

(2) INFORMATION FOR SEQ ID NO:43:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:43:

TGGAATGAAT TCGAAGATGA ACTGACGTTC TAT                                        33

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:44:

AGGAAACTGA CGGCGACCCT GAAAACCCTT                                            30

(2) INFORMATION FOR SEQ ID NO:45:

(i) SEQUENCE CHARACTERISTICS:
        (A) LENGTH: 596 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..435

(xi) SEQUENCE DESCRIPTION: SEQ ID NO:45:

ATG ACC ATG ATT ACG AAT TCC CGG GGA TCC GTC GAC GCT CCC ATG ACC             48
Met Thr Met Ile Thr Asn Ser Arg Gly Ser Val Asp Ala Pro Met Thr
 1               5                  10                  15

CAG ACA ACG CCC TTG AAG ACA AGC TGG GTT AAC TGC TCT AAC ATG ATC             96
Gln Thr Thr Pro Leu Lys Thr Ser Trp Val Asn Cys Ser Asn Met Ile
             20                  25                  30

GAT GAA ATT ATA ACA CAC TTA AAG CAG CCA CCT TTG CCT TTG CTG GAC            144
Asp Glu Ile Ile Thr His Leu Lys Gln Pro Pro Leu Pro Leu Leu Asp
         35                  40                  45

TTC AAC AAC CTC AAT GGG GAA GAC CAA GAC ATT CTG ATG GAA AAT AAC            192
Phe Asn Asn Leu Asn Gly Glu Asp Gln Asp Ile Leu Met Glu Asn Asn
     50                  55                  60

CTT CGA AGG CCA AAC CTG GAG GCA TTC AAC AGG GCT GTC AAG AGT TTA            240
Leu Arg Arg Pro Asn Leu Glu Ala Phe Asn Arg Ala Val Lys Ser Leu
 65                  70                  75                  80

CAG AAC GCA TCA GCA ATT GAG AGC ATT CTT AAA AAT CTC CTG CCA TGT            288
Gln Asn Ala Ser Ala Ile Glu Ser Ile Leu Lys Asn Leu Leu Pro Cys
                 85                  90                  95

CTG CCC CTG GCC ACG GCC GCA CCC ACG CGA CAT CCA ATC CAT ATC AAG            336
Leu Pro Leu Ala Thr Ala Ala Pro Thr Arg His Pro Ile His Ile Lys
            100                 105                 110

GAC GGT GAC TGG AAT GAA TTC CGG AGG AAA CTG ACG TTC TAT CTG AAA            384
Asp Gly Asp Trp Asn Glu Phe Arg Arg Lys Leu Thr Phe Tyr Leu Lys
        115                 120                 125

ACC CTT GAG AAT GCG CAG GCT CAA CAG ACG ACT TTG AGC CTC GCG ATC            432
Thr Leu Glu Asn Ala Gln Ala Gln Gln Thr Thr Leu Ser Leu Ala Ile
    130                 135                 140
```

```
TTT TGAGTCCAAC GTCCAGCTCG TTCTCTGGGC CTTCTCACCA CAGAGCCTCG      485
Phe
145

GTCGAGTTTT AAACTGGTTC CTAGGGATGT GTGAGAATAA ACTAGACTCT GAACAAAAAA    545

AAAAAAAAAA AAAAAAAAAA AAAAAACCG AATTCCCGGG GATCTAAACT T           596
```

(2) INFORMATION FOR SEQ ID NO:46:

(i) SEQUENCE CHARACTERISTICS:
       (A) LENGTH: 145 amino acids
       (B) TYPE: amino acid
       (D) TOPOLOGY: linear (ii) MOLECULE TYPE: protein (xi) SEQUENCE DESCRIPTION: SEQ ID NO:46:

```
Met Thr Met Ile Thr Asn Ser Arg Gly Ser Val Asp Ala Pro Met Thr
 1               5                  10                  15

Gln Thr Thr Pro Leu Lys Thr Ser Trp Val Asn Cys Ser Asn Met Ile
                20                  25                  30

Asp Glu Ile Ile Thr His Leu Lys Gln Pro Pro Leu Pro Leu Leu Asp
            35                  40                  45

Phe Asn Asn Leu Asn Gly Glu Asp Gln Asp Ile Leu Met Glu Asn Asn
         50                  55                  60

Leu Arg Arg Pro Asn Leu Glu Ala Phe Asn Arg Ala Val Lys Ser Leu
 65                  70                  75                  80

Gln Asn Ala Ser Ala Ile Glu Ser Ile Leu Lys Asn Leu Leu Pro Cys
                 85                  90                  95

Leu Pro Leu Ala Thr Ala Ala Pro Thr Arg His Pro Ile His Ile Lys
                100                 105                 110

Asp Gly Asp Trp Asn Glu Phe Arg Arg Lys Leu Thr Phe Tyr Leu Lys
            115                 120                 125

Thr Leu Glu Asn Ala Gln Ala Gln Gln Thr Thr Leu Ser Leu Ala Ile
        130                 135                 140
Phe
145
```

(2) INFORMATION FOR SEQ ID NO:47:

(i) SEQUENCE CHARACTERISTICS:
       (A) LENGTH: 86 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 1..60

(xi) SEQUENCE DESCRIPTION: SEQ ID NO:47:

```
ATG ACC ATG ATT ACG AAT TCC CGG GGA TCC TCT GCA GCA GCG GCG GCT    48
Met Thr Met Ile Thr Asn Ser Arg Gly Ser Ser Ala Ala Ala Ala Ala
 1               5                  10                  15

CTC GCG ATC TTT TGACTCGAGT AGAAGAGAAG AGAATC                       86
Leu Ala Ile Phe
            20
```

(2) INFORMATION FOR SEQ ID NO:48:

(i) SEQUENCE CHARACTERISTICS:
       (A) LENGTH: 20 amino acids
       (B) TYPE: amino acid -continued

```
        (D) TOPOLOGY: linear (ii) MOLECULE TYPE: protein (xi) SEQUENCE DESCRIPTION: SEQ ID NO:48:

Met Thr Met Ile Thr Asn Ser Arg Gly Ser Ser Ala Ala Ala Ala Ala
 1               5                  10                  15

Leu Ala Ile Phe
            20
```